United States Patent
Jensen et al.

(10) Patent No.: US 11,403,732 B2
(45) Date of Patent: Aug. 2, 2022

(54) ULTRASOUND SUPER RESOLUTION IMAGING

(71) Applicant: B-K Medical ApS, Herlev (DK)

(72) Inventors: Jorgen Arendt Jensen, Horsholm (DK); Iman Taghavi, Kongens Lyngy (DK)

(73) Assignee: B-K Medical APS, Herlev (DK)

( * ) Notice: Subject to any disclaimer, the term of this patent is extended or adjusted under 35 U.S.C. 154(b) by 201 days.

(21) Appl. No.: 16/929,398

(22) Filed: Jul. 15, 2020

(65) Prior Publication Data
US 2021/0407043 A1  Dec. 30, 2021

Related U.S. Application Data

(60) Provisional application No. 63/043,839, filed on Jun. 25, 2020.

(51) Int. Cl.
*G06T 3/40* (2006.01)
*A61B 8/08* (2006.01)
(Continued)

(52) U.S. Cl.
CPC ............ *G06T 3/4053* (2013.01); *A61B 8/14* (2013.01); *A61B 8/481* (2013.01); *A61B 8/5246* (2013.01);
(Continued)

(58) Field of Classification Search
CPC ..... G06T 3/4053; G06T 5/002; G06T 7/0012; G06T 7/20; G06T 7/70;
(Continued)

(56) References Cited

U.S. PATENT DOCUMENTS

| 2016/0051233 A1* | 2/2016 | Mo ...................... G01S 15/8979 600/447 |
| 2016/0157828 A1* | 6/2016 | Sumi .................... G01N 29/46 702/189 |

FOREIGN PATENT DOCUMENTS

| WO | WO-2016067253 A1 * | 5/2016 | ......... G01S 15/8915 |
| WO | WO-2020141127 A1 * | 7/2020 | ............. A61B 8/085 |

OTHER PUBLICATIONS

Sevan Harput, et al., Two-Stage Motion Correction for Super Resolution Ultrasound Imaging in Human Lower Limb, IEEE Transactions on Ultrasonics, Ferroelectrics and Frequency Control, vol. 65, No. 5, May 2018.

(Continued)

*Primary Examiner* — Siamak Harandi
(74) *Attorney, Agent, or Firm* — Daugherty & Del Zoppo Co., LPA

(57) ABSTRACT

An apparatus includes a processor and a display. The processor includes a combiner configured to combine contrast data acquired with a same sub-aperture, for each of a plurality of sub-apertures, to create a contrast frame for each of the sub-apertures. The processor includes a microbubble detector configured to determine positions of microbubbles in the contrast frames. The processor includes a motion estimator configured to estimate a motion field based on frames of B-mode data for each of the plurality of sub-apertures. The processor includes a motion corrector configured to motion correct the positions of the microbubbles in the contrast frames based on the motion field and time delays between emissions for the sets of contrast data and the emission for B-mode data, for each of the plurality of sub-apertures, to produce motion corrected contrast frames. The display is configured to display the motion corrected contrast frames as super resolution images.

20 Claims, 2 Drawing Sheets

(51) Int. Cl.
    *G06T 7/20*          (2017.01)
    *G06T 7/00*          (2017.01)
    *G06T 7/70*          (2017.01)
    *G06T 5/00*          (2006.01)
    *A61B 8/14*          (2006.01)

(52) U.S. Cl.
    CPC ............ *A61B 8/5276* (2013.01); *G06T 5/002* (2013.01); *G06T 7/0012* (2013.01); *G06T 7/20* (2013.01); *G06T 7/70* (2017.01); *G06T 2207/10132* (2013.01); *G06T 2207/30004* (2013.01)

(58) Field of Classification Search
    CPC . G06T 2207/10132; G06T 2207/30004; A61B 8/14; A61B 8/481; A61B 8/5246; A61B 8/5276
    See application file for complete search history.

(56) References Cited

OTHER PUBLICATIONS

Thomas M. Kierski, et al., Superharmonic Ultrasound for Motion-Independent Localization Microscopy: Applications to Microvascular Imaging From Low to High Flow Rates, IEEE Transactions on Ultrasonics, Ferroelectrics and Frequency Control, vol. 67, No. 5, May 2020.

Shanshan Tang, et al., Kalman Filter-Based Microbubble Tracking for Robust Super-Resolution Ultrasound Microvessel Imaging, DOI 10.1109/TUFFC.2020.2984384, IEEE Transactions on Ultrasonics, Ferroelectrics and Frequency Control. Downloaded on Jun. 4, 2020 from IEEE Xplore.

\* cited by examiner

ULTRASOUND SUPER RESOLUTION IMAGING

TECHNICAL FIELD

The following generally relates to ultrasound and more particularly to ultrasound super resolution imaging.

BACKGROUND

Super resolution imaging is a technique to enhance a resolution of an image. Ultrasound super resolution imaging relies on tracking microbubbles of a microbubble based contrast agent to visualize microvasculature. However, tissue motion, e.g., from breathing, the heart beating, muscle contracting, etc., that is larger than a size of microvasculature limits the resolution of the super resolution image. For example, motion in the range of 100-200 µm in both the axial and lateral directions would limit the resolution of the ultrasound super resolution image to 100-200 µm, and vessels smaller than 100-200 µm such as microvasculature (e.g., 10 µm), would not be visible.

One motion correction scheme excludes frames with higher motion. (See J. Foiret et al., "Ultrasound localization microscopy to image and assess microvasculature in a rat kidney," Scientific Reports, vol. 7, no. 1, pp. 13 662:1-12, 2017). Another scheme combines ultrasound microscopy and dual-frequency imaging, but the B-mode frame rate is only sufficient to capture motion from breathing and more rapid movements (e.g., a beating heart) are discarded. (See T. M. Kierski et al., "Superharmonic ultrasound for motion-independent localization microscopy: Applications to microvascular imaging from low to high flow rates," IEEE Trans. Ultrason., Ferroelec., Freq. Contr., vol. 67, no. 5, pp. 957-967, 2020).

Unfortunately, the above and other approaches do not address spatial and temporal differences between the motion estimates from the B-mode frames and the contrast frames. As such, there is an unresolved need for an improved approach to super resolution imaging.

SUMMARY

Aspects of the application address the above matters, and others.

In one aspect, an apparatus included a processor and a display. The processor includes a combiner configured to combine sets of contrast data acquired with a same sub-aperture, for each of a plurality of sub-apertures, to create a contrast frame for each of the sub-apertures. The processor further includes a microbubble detector configured to determine positions of microbubbles in the contrast frames. The processor further includes a motion estimator configured to estimate a motion field based on frames of B-mode data for each of the plurality of sub-apertures. The processor further includes a motion corrector configured to motion correct the positions of the microbubbles in the contrast frames based on the motion field and time delays between emissions for the sets of contrast data and the corresponding emission for B-mode data, for each of the plurality of sub-apertures, to produce motion corrected contrast frames. The display is configured to visually display the motion corrected contrast frames, wherein the motion corrected contrast frames include super resolution images.

In another aspect, a method includes combining sets of contrast data acquired with a same sub-aperture, for each of a plurality of sub-apertures, to create a contrast frame for each of the sub-apertures. The method further includes determining positions of microbubbles in the contrast frames. The method further includes estimating a motion field based on frames of B-mode data for each of the plurality of sub-apertures. The method further includes motion correcting the positions of the microbubbles in the contrast frames based on the motion field and time delays between emissions for the sets of contrast data and the corresponding emission for B-mode data, for each of the plurality of sub-apertures, to produce motion corrected contrast frames. The method further includes displaying the motion corrected contrast frames, wherein the motion corrected contrast frames include super resolution images.

In yet another aspect, a computer-readable storage medium storing instructions that when executed by a computer cause the computer to: combine sets of contrast data acquired with a same sub-aperture, for each of a plurality of sub-apertures, to create a contrast frame for each of the sub-apertures, determine positions of microbubbles in the contrast frames, estimate a motion field based on frames of B-mode data for each of the plurality of sub-apertures, motion correcting the positions of the microbubbles in the contrast frames based on the motion field and time delays between emissions for the sets of contrast data and the corresponding emission for B-mode data, for each of the plurality of sub-apertures, to produce motion corrected contrast frames, and display the motion corrected contrast frames, wherein the motion corrected contrast frames include super resolution images.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
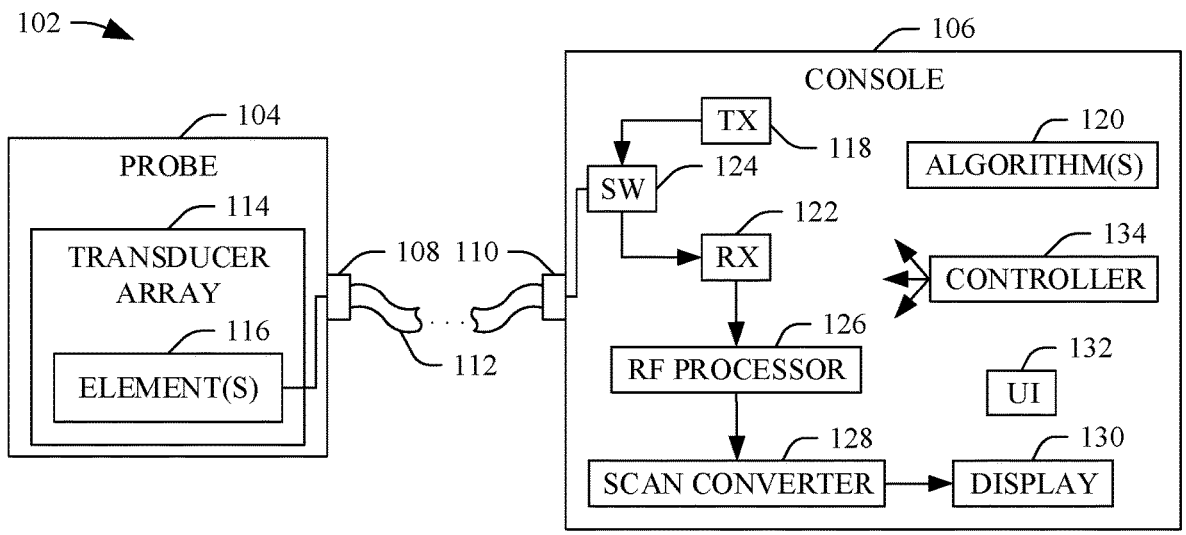
FIG. 1 diagrammatically illustrates an example ultrasound system configured to generate super resolution images, in accordance with an embodiment(s) herein.

FIG. 1 illustrates an example imaging system 102 such as an ultrasound imaging system/scanner. The imaging system 102 includes a probe 104 and a console 106, which interface with each other through suitable complementary hardware (e.g., cable connectors 108 and 110 and a cable 112 as shown, etc.) and/or wireless interfaces (not visible).

The probe 104 includes a transducer array 114 with one or more transducer elements 116. The transducer array 114 includes a one or two dimensional (1 or 2-D), linear, curved and/or otherwise shaped, fully populated or sparse, etc. array. The elements 116 are configured to convert excitation electrical pulses into an ultrasound pressure field and a received ultrasound pressure field (echo) into an electrical (e.g., a radio frequency (RF)) signal. Generally, the received pressure field is in response to the transmitted pressure field interacting with matter, e.g., contrast agent microbubbles, tissue, etc.

The console 106 includes transmit circuitry (TX) 118 configured to generate the excitation electrical pulses based on an algorithm(s) 120. For B-mode imaging, a suitable acquisition results in data that can be used to detect the linear signals from tissue (i.e. tissue data). For contrast-enhanced imaging using a contrast agent with microbubbles (which is administered to a subject prior to and/or during the scan), a suitable acquisition results in data that can be used to detect non-linear signals from the microbubbles (i.e. contrast data) and suppress the linear signals.

Figure 2:
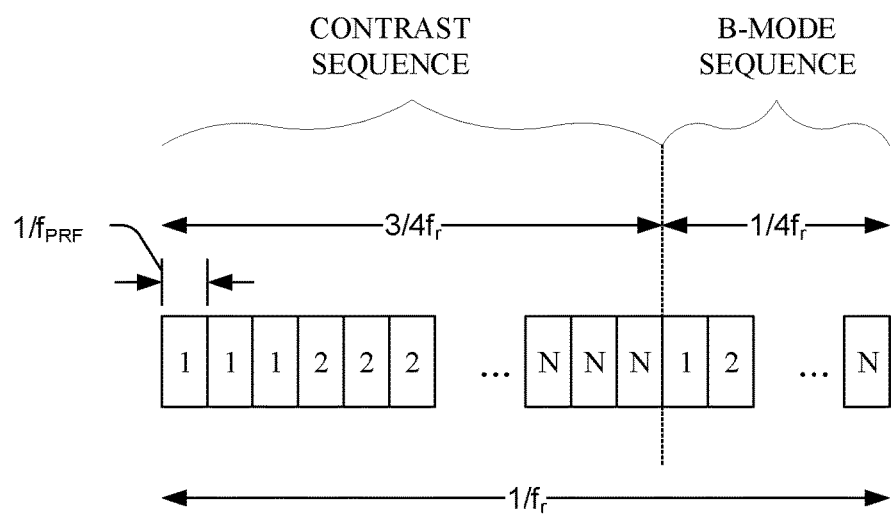
FIG. 2 illustrates an example contrast-enhanced imaging acquisition sequence for the system of FIG. 1, in accordance with an embodiment(s) described herein.

Briefly turning to FIG. 2, an example algorithm is illustrated. In this example, the algorithm is a contrast-enhanced imaging acquisition amplitude modulation algorithm. In FIG. 2, $f_{prf}$ represents a pulse repetition frequency, and $f_r$ represents an imaging framerate frequency of a complete sequence, i.e. contrast+B-mode ($4Nf_{prf}$ in FIG. 2). The illustrated contrast-enhanced imaging acquisition amplitude modulation algorithm includes a sliding aperture of k elements, where k is an integer greater than zero. N represents a number of the sub-apertures of the sliding aperture.

For contrast data, a first sub-aperture emits three times, one with full amplitude and two with half amplitude. This is shown in FIG. 2 as three sub-aperture emission 1, 1 and 1. The sub-aperture then slides to a next position and again emits three times. This is shown in FIG. 2 as three sub-aperture emission 2, 2 and 2. This is repeated for the remaining N sub-apertures. For B-mode data, each of the N sub-apertures emits only once (1, 2, ..., N). A time delay between contrast emissions (e.g., 1, 1 and 1) and the corresponding B-mode emission (e.g., 1) for a sub-aperture varies from $f_r/4$ to $3f_r/4$.

Returning to FIG. 1. the console 106 further includes receive circuitry (RX) 122 configured to process the RF signals, e.g., amplify, digitize, and/or otherwise process the RF signals. For the contrast data, the received echoes for each of the three emission provide data for enhancing the non-linear signal/microbubbles. For the B-mode data, the received echoes for each of the single emissions provide data for enhancing the linear signal/tissue.

The console 106 further includes a switch (SW) 124 configured to switch between the TX 118 and RX 122 for transmit and receive operations, e.g., by electrically connecting and electrically disconnecting the TX 118 and RX 122. In a variation, separate switches are utilized to switch between the TX 118 and RX 122.

The console 106 includes further an RF processor 126. The RF processor 126 is configured to process the contrast and B-mode data to create ultrasound super resolution images. As described in greater detail below, creating contrast frames, detecting microbubbles in the contrast frames, estimating a local motion field from the B-mode frames, motion correcting the position of the microbubbles based on the local motion estimation, and registering the microbubbles across the contrast frames.

Generally, this approach utilizes a full motion field that is estimated as a function of space and time from all B-mode frames to co-register estimated tracks of microbubbles to a reference frame. In one instance, this ensures that no frame is skipped. In addition, this approach can reduce microbubble localization uncertainty relative to a configuration that does not utilize this approach.

The console 106 further includes a scan converter 128 and a display 130. The scan converter 128 is configured to scan convert the motion corrected contrast frames and/or B-mode frames for display, e.g., by converting the motion corrected contrast frames and/or the B-mode frames to the coordinate system of the display 130. The display 130 can display a motion corrected contrast frame and/or a B-mode frame alternately or concurrently, e.g., next to each other and/or on combined.

The console 106 further includes a user interface 132, which includes one or more input devices (e.g., a button, a touch pad, a touch screen, etc.) and one or more output devices (e.g., a display screen, a speaker, etc.). The console 106 further includes a controller 134 configured to control one or more of the transmit circuitry 118, the receive circuitry 122, the switch 124, the RF processor 126, the scan converter 128, the display 130, and/or the user interface 132.

It is to be appreciated that at least the RF processor 126 can be implemented by a hardware processor (e.g., a central processing unit (CPU), graphics processing unit (GPU), a microprocessor, etc.) executing computer readable instructions encoded or embedded on computer readable storage medium, which excludes transitory medium.

Figure 3:
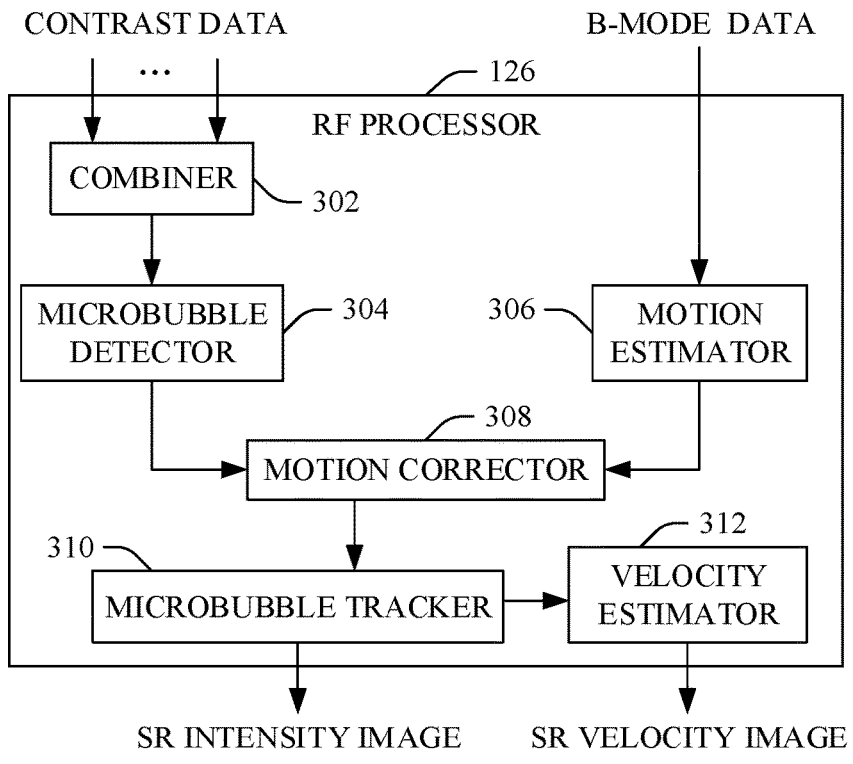
FIG. 3 diagrammatically illustrates an example configuration of the processor of the ultrasound system of FIG. 1, in accordance with an embodiment(s) described herein.

FIG. 3 diagrammatically illustrates an example configuration of the RF processor 126.

The RF illustrated processor includes a combiner 302. The combiner 302 is configured to combine the contrast data from the three emissions for each a sub-aperture to generate a contrast frame for the sub-aperture, for each of the sub-apertures. In one instance, this includes subtracting the data for the half amplitude acquisitions from the data for the full amplitude acquisition. Other approaches are also contemplated herein.

The RF processor further includes a microbubble detector 304. The microbubble detector 304 is configured to determine a centroid (or other region) of each of the microbubbles in each of the contrast frames. In one instance, this includes signal-to-noise (SNR) enhancement followed by microbubble localization. For SNR Enhancement, suitable approaches include thresholding, spatial filtering (e.g. Gaussian, Laplacian of Gaussian, etc.), spatio-temporal filtering, model fitting, and/or other approaches. For localization, suitable approaches include peak detection, centroid estimation (e.g. weighted centroid, etc.), learning-based, and/or other approaches.

The RF processor further includes a motion estimator 306. The motion estimator 306 is configured to process the B-mode frames to estimate tissue motion. In one instance, this includes using speckle tracking on the envelope data. An example of speckle tracking can be found in G. E. Trahey et al.," IEEE Trans. Biomed. Eng., vol. BME-34, no. 12, pp. 965-967, 1987. For local motion estimation, each B-mode frame is divided into a plurality of partially overlapping sub-regions, with one of the frames being identified as a reference frame. Examples of suitable sub-region sizes include, but are not limited to, 1×1 to 10×10 millimeters square (mm²), larger, smaller, non-square, etc. Examples of a suitable B-mode reference frame includes a B-mode frame near the middle B-mode frame and/or other B-mode frame. In another instance, more than one B-mode reference frame is utilized.

The motion estimator 306 cross-correlates each sub-region in the B-mode reference frame with the corresponding sub-region in the other B-mode frames, and motion in the axial and lateral directions is estimated. The estimated motion for each sub-region is assigned to a center (and/or other location) of the corresponding sub-region, and the collection of motion estimates for a frame provides a discrete motion field through that frame. The estimated displacements vary spatially and temporally. Motion can be estimated at any point in any frame (i.e. space and/or time) using interpolation such a 3-D spline, etc. on the 3-D motion field.

The RF processor further includes a motion corrector 308. The motion corrector 308 is configured to apply the local motion estimates on the detected microbubble locations. By way of non-limiting example, for a detected microbubble in the kth frame at position $\hat{\vec{r}} = (z_0, x_0)$, the correct position $\hat{\vec{r}}$ of the microbubble can be approximated as shown in Equation 1:

$$\hat{\vec{r}} \approx \vec{r} - \vec{M}(t, \vec{r}),\qquad\text{Equation 1:}$$

where $\vec{M}(t, \vec{r})$ represents the motion field, $$t = \frac{k-1}{f_r} - t_d(n, m),$$

where k represents the frame position, $f_r$ represents the imaging framerate frequency, and $t_d(n, m)$ represents a time difference between an nth line of a contrast frame and an mth line of the corresponding B-mode frame. In one instance, e.g., in FIG. 2, $t_d(n, m)$ is determined as shown in Equation 2:

$$t_d(n, m) = \frac{3N_{lines} - 3n + m + 1}{f_{prf}},\qquad\text{Equation 2}$$

where n, m ∈ {1, 2, ..., $N_{lines}$}, $N_{lines}$ represents a number of lines in the frame, and $f_{prf}$ represents the pulse repetition frequency.

The position of the detected microbubble at $\vec{r} = (z_0, x_0)$ in the kth frame can be expressed as a function of the corrected microbubble position and value of the motion field at that position and time as shown in Equation 3:

$$\vec{r} = \hat{\vec{r}} + \vec{M}\left(\frac{k-1}{f_r} - t_d(\hat{n}, m), \hat{\vec{r}}\right),\qquad\text{Equation 3}$$

where $\hat{\vec{r}} = (\hat{z}_0, \hat{x}_0)$ and $\hat{n}$ are the unknown correct position and its relative image line in the contrast image, respectively. In one instance, $\hat{\vec{r}}$ is computed using an optimization techniques such as a least-squares optimization as shown in Equation 4:

$$[\hat{\vec{r}}, \hat{n}] = \underset{\vec{p},q}{\operatorname{argmin}}\left\|\vec{p} - \vec{r} + \vec{M}\left(\frac{k-1}{f_r} - t_d(q, m), \vec{p}\right)\right\|_2^2.\qquad\text{Equation 4}$$

where $\vec{p}$ and q are arguments.

An example algorithm for solving Equation 4 is provided next.

---

Initialization:
    $N_{itr} = 0$,
    $\hat{\vec{r}} = \vec{r}$
    $\hat{n} = m = (x_0 - x_{min}) / dx$, where $x_{min}$ and dx are a minimum lateral position and a lateral pixel size of the frame.
1:  while (error ≥ $e_{max}$) or ($N_{itr} \le N_{max}$) do 2:     Calculate a time delay between the mth line of the B-mode frame and the $\hat{n}$th line of the contrast frame $$t_d(\hat{n}, m) = \frac{3N_{lines} - 3\hat{n} + m + 1}{f_{prf}}.$$

3:     Update the position of the estimated microbubble $$\hat{\vec{r}} \approx \vec{r} - \vec{M}\left(\frac{k-1}{f_r} - t_d(\hat{n}, m), \vec{r}\right).$$

4:     Update $\hat{n}$ $$\hat{n} = \frac{x_{lines(1)} - \hat{x}_0}{dx}.$$

5:     Calculate assignment error $$\text{error} = \left\|\hat{\vec{r}} - \vec{r} + \vec{M}\left(\frac{k-1}{f_r} - t_d(\hat{n}, m), \hat{\vec{r}}\right)\right\|2.$$

6:     Update iteration
       $N_{itr} = N_{itr} + 1$.
7:  end while

---

In general, the motion corrector 308 iteratively assigns motion estimates by calculating a time delay between each an image line of a contrast frame and an image line of the B-mode frame for a sub-aperture (the three emissions of the contrast sequence corresponded to the same image line as one emission in the B-mode sequence), updating a position of an estimated bubble in the contrast frame based on the motion field and the time delay, updating the image line in the contrast frame, and repeating the above until stopping criteria is satisfied or the maximum number of iterations is reached.

The RF processor further includes a microbubble tracker 310. The microbubble tracker 310 is configured to generate tracks that link microbubbles from frame to frame. Suitable approaches include, but are not limited to, nearest-neighbor, multi-frame data structure, dynamic programming, combinatorial, multi hypothesis, explicit motion models (e.g. Kalman filtering), learning-based, and/or other techniques. Provided herein is an example approach based on Kalman filtering.

This approach can be modeled as $\vec{r}(t) = \vec{r}(t-1) + d\vec{r}(t) + \varepsilon(t)$, where $\vec{r}(t) = (r_z(t), r_x(t))$ represents the position of a microbubble at time t, $d\vec{r}(t) = (dr_z(t), dr_x(t))$ represents the displacement of the microbubble, and $\varepsilon(t)$ represents an uncertainty in the displacement. This model can be formulated, e.g., within the Kalman framework as shown below:

$$\begin{cases}\text{Prediction State: } \bar{x}(t) = Fx(t-1) + \varepsilon(t) \\ \text{Observation State: } \bar{z}(t) = H\bar{x}(t) + v(t)\end{cases}, \text{where}$$

$$x(t) = [\vec{r}(t), d\vec{r}(t)]^T = [r_z(t), r_x(t), dr_z(t), dr_x(t)]^T,$$

$$F = \begin{bmatrix} 1 & 0 & 1 & 0 \\ 0 & 1 & 0 & 1 \\ 0 & 0 & 1 & 0 \\ 0 & 0 & 0 & 1 \end{bmatrix},$$

$$H = \begin{bmatrix} 1 & 0 & 0 & 0 \\ 0 & 1 & 0 & 0 \end{bmatrix},$$

-continued $\varepsilon(t) \sim \mathcal{N}(0, \sigma_\varepsilon^2)$, and $v(t) \sim \mathcal{N}(0, \sigma_v^2)$.

When entering the blood stream, the microbubbles have uncontrolled concentrations as well as different velocities and flow dynamics in different parts of the kidney. To track these different scenarios, a hierarchical structure of Kalman filters is utilized. Table 1 shows examples parameters for a hierarchical structure of Kalman filter.

TABLE 1

Examples parameters for a hierarchical structure of Kalman filter.

| Level | 1 | 2 | 3 | 4 | 5 |
|---|---|---|---|---|---|
| Velocity (mm/s) | 0-3 | 3-6 | 6-9 | 9-12 | 12-15 |
| $\sigma_\varepsilon$ | 0.006 | 0.012 | 0.018 | 0.024 | 0.03 |
| $\sigma_v$ | 0.025 | 0.0125 | 0.00625 | 0.003125 | 0.0015 |
| Max Linking | $6/f_r$ | $12/f_r$ | $18/f_r$ | $24/f_r$ | $15/f_r$ |
| Gap-closing | 3 | 2 | 2 | 1 | 1 |

At each level in Table 1, a Kalman filter is applied to the remaining untracked microbubbles from the previous levels. The tracked microbubbles at deeper levels have higher velocities. A maximum linking distance is a maximum acceptable distance between the estimated microbubble position by the Kalman filter and the nearest motion-corrected microbubble position in the next frame. Linking of multiple microbubbles can be performed using Hungarian assignment. If a microbubble is miss-detected over a couple of frames, the Kalman filter can predict its trajectory based on its previous detected positions. The gap closing parameter is a number of frames a microbubble can be miss-detected.

The motion-corrected and linked microbubbles provide ultrasound super resolution intensity image. In the illustrated embodiment, the RF processor 126 includes a velocity estimator 312 configured to process track locations to generate a super resolution velocity image. By way of non-limiting example, the velocity estimator 312 can be configured to determine a time derivative of track locations, which yields both the axial and lateral velocities. An axial and a lateral velocity image can then be constructed by drawing anti-aliased velocity weighted lines at the track positions. A mean velocity at each pixel in the velocity images can be found by dividing with a weighting image if it was different from zero. A Vector Flow Image (VFI) of the microbubble can be generated by combining the axial and lateral velocity images. In another instance, the velocity estimator 312 is omitted.

It is to be appreciated that the hierarchical tracking approach described herein provides a better visualization of opposite flows and improved flow quantification, relative to a configuration that does not employ the hierarchical tracking approach. The ultrasound super resolution intensity and/or velocity images can be displayed via the display 130.

Figure 4:
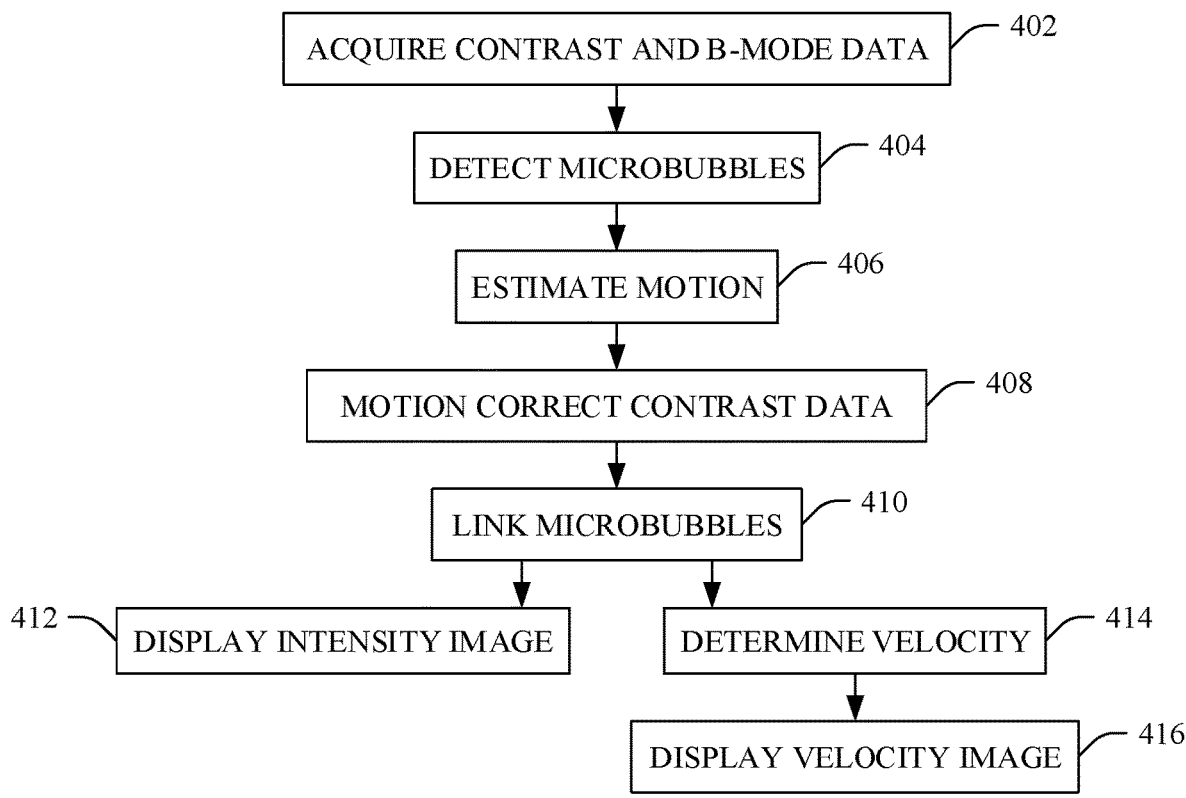
FIG. 4 illustrates an example method, in accordance with an embodiment(s) herein.

FIG. 4 illustrates an example method in accordance with an embodiment herein.

The ordering of the following acts is for explanatory purposes and is not limiting. As such, one or more of the acts can be performed in a different order, including, but not limited to, concurrently. Furthermore, one or more of the acts may be omitted and/or one or more other acts may be added.

At 402, contrast and B-mode data are acquired, as described herein and/or otherwise.

At 404, microbubbles are detected in the contrast data, as described herein and/or otherwise.

At 406, motion is estimated from the B-mode data, as described herein and/or otherwise.

Although act 404 is described before act 406, it is to be understood that act 404 can be performed before act 406 or in parallel with act 406.

At 408, the microbubbles in the contrast data are motion corrected based on the estimated motion, as described herein and/or otherwise.

At 410, the microbubble are linked between frames of the contrast data, creating a super resolution intensity image, as described herein and/or otherwise.

At 412, the super resolution intensity image is displayed, as described herein and/or otherwise.

At 414, a vector velocity is determined, as described herein and/or otherwise.

At 416, a super resolution vector velocity image is displayed, as described herein and/or otherwise.

The above may be implemented by way of computer readable instructions, encoded or embedded on computer readable storage medium (which excludes transitory medium), which, when executed by a computer processor(s) (e.g., central processing unit (CPU), microprocessor, etc.), cause the processor(s) to carry out acts described herein. Additionally, or alternatively, at least one of the computer readable instructions is carried by a signal, carrier wave or other transitory medium (which is not computer readable storage medium).

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An apparatus, comprising:
    a processor, including:
      a combiner configured to combine sets of contrast data acquired with a same sub-aperture, for each of a plurality of sub-apertures, to create a contrast frame for each of the sub-apertures;
      a microbubble detector configured to determine positions of microbubbles in the contrast frames;
      a motion estimator configured to estimate a motion field based on frames of B-mode data for each of the plurality of sub-apertures; and
      a motion corrector configured to motion correct the positions of the microbubbles in the contrast frames based on the motion field and time delays between emissions for the sets of contrast data and the corresponding emission for B-mode data, for each of the plurality of sub-apertures, to produce motion corrected contrast frames; and
    a display configured to visually display the motion corrected contrast frames, wherein the motion corrected contrast frames include super resolution images.

2. The apparatus of claim 1, wherein the motion corrector iteratively assigns motion estimates by:
    1) calculating a time delay between each an image line of a contrast frame and an image line of the B-mode frame for a same sub-aperture;

2) updating a position of an estimated bubble in the contrast frame based on the motion field and the time delay;
3) updating the image line in the contrast frame; and
  repeating 1), 2) and 3) until stopping criteria is satisfied.

3. The apparatus of claim 1, wherein the processor further comprises:
a microbubble tracker configured to link the microbubbles from frame to frame across the motion corrected contrast frames to produce the super resolution images.

4. The apparatus of claim 3, wherein the processor links the microbubbles across the motion corrected contrast frames based on hierarchical tracking.

5. The apparatus of claim 1, wherein the microbubble detector extracts a centroid of a microbubble to determine a position of the microbubble in a contrast frame.

6. The apparatus of claim 5, wherein the microbubble detector extracts the centroid of the microbubble by enhancing a signal-to-noise ratio of the frame and then localizing the centroid in the signal-to-noise ratio enhanced frame.

7. The apparatus of claim 1, wherein the motion estimator determines the motion field using speckle tracking on envelope data.

8. The apparatus of claim 1, wherein the motion estimator cross-correlates each of a plurality of sub-regions of a reference B-mode frame with corresponding sub-regions in the other B-mode frames, and motion in axial and lateral directions is determined.

9. The apparatus of claim 8, wherein the sub-regions are partially overlapping sub-regions.

10. The apparatus of claim 8, wherein the motion estimator assigns a motion estimate for a sub-region to a center region of the sub-region, and a collection of all of the motion estimates for all of the sub-regions of a frame is a discrete motion field through the frame.

11. The apparatus of claim 1, wherein the super resolution images includes an intensity super resolution image.

12. The apparatus of claim 1, wherein the super resolution images includes a velocity super resolution image.

13. The apparatus of claim 1, further comprising:
a transducer array configured to transmit an ultrasound pressure field and receive an echo pressure field for a contrast-enhanced scan to acquire the contrast data and the B-mode data.

14. The apparatus of claim 13, wherein the processor is configured employ a pulse amplitude modulation sequence to acquire the contrast data and the B-mode data.

15. A method, comprising:
combining sets of contrast data acquired with a same sub-aperture, for each of a plurality of sub-apertures, to create a contrast frame for each of the sub-apertures;
determining positions of microbubbles in the contrast frames;
estimating a motion field based on frames of B-mode data for each of the plurality of sub-apertures;
motion correcting the positions of the microbubbles in the contrast frames based on the motion field and time delays between emissions for the sets of contrast data and the corresponding emission for B-mode data, for each of the plurality of sub-apertures, to produce motion corrected contrast frames; and
displaying the motion corrected contrast frames, wherein the motion corrected contrast frames include super resolution images.

16. The method of claim 15, further comprising:
1) calculating a time delay between an image line of a contrast frame and an image line of the B-mode frame for a same sub-aperture;
2) updating a position of an estimated bubble in the contrast frame based on the motion field and the time delay;
3) updating the image line in the contrast frame; and
  repeating 1), 2) and 3) until stopping criteria is satisfied.

17. The method of claim 15, further comprising:
linking the microbubbles across the motion corrected contrast frames to produce
the super resolution images via a hierarchical tracking.

18. A computer-readable storage medium storing instructions that when executed by a computer cause the computer to:
combine sets of contrast data acquired with a same sub-aperture, for each of a plurality of sub-apertures, to create a contrast frame for each of the sub-apertures;
determine positions of microbubbles in the contrast frames;
estimate a motion field based on frames of B-mode data for each of the plurality of sub-apertures; and
motion correcting the positions of the microbubbles in the contrast frames based on the motion field and time delays between emissions for the sets of contrast data and the corresponding emission for B-mode data, for each of the plurality of sub-apertures, to produce motion corrected contrast frames.

19. The computer-readable storage medium of claim 18, wherein, for microbubble position determination and motion correcting the positions, the instructions cause the computer to:
1) calculate a time delay between an image line of a contrast frame and an image line of the B-mode frame for a same sub-aperture;
2) update a position of an estimated bubble in the contrast frame based on the motion field and the time delay;
3) update the image line in the contrast frame; and
  repeating 1), 2) and 3) until stopping criteria is satisfied.

20. The computer-readable storage medium of claim 18, wherein the instructions further cause the computer to:
link the microbubbles across the motion corrected contrast frames to produce a super resolution images via a hierarchical tracking; and
display the super resolution image.

* * * * *